United States Patent
Chiu et al.

(10) Patent No.: US 10,894,873 B2
(45) Date of Patent: Jan. 19, 2021

(54) ULTRAVIOLET ABSORBING COMPOUND AND APPLICATIONS THEREOF

(71) Applicant: CHITEC TECHNOLOGY CO., LTD., Taipei (TW)

(72) Inventors: Chingfan Chris Chiu, Taipei (TW); Wei-Chun Chang, Taipei (TW); Huang-Min Wu, Taipei (TW); Yi-Shuo Huang, Taipei (TW)

(73) Assignee: CHITEC TECHNOLOGY CO., LTD., Taipei (TW)

( * ) Notice: Subject to any disclaimer, the term of this patent is extended or adjusted under 35 U.S.C. 154(b) by 82 days.

(21) Appl. No.: 16/414,589

(22) Filed: May 16, 2019

(65) Prior Publication Data

US 2019/0390040 A1  Dec. 26, 2019

(30) Foreign Application Priority Data

Jun. 26, 2018 (TW) .............................. 107121886 A

(51) Int. Cl.
*C08K 5/1545* (2006.01)
*C07D 493/10* (2006.01)
*C08K 5/00* (2006.01)

(52) U.S. Cl.
CPC .......... *C08K 5/1545* (2013.01); *C07D 493/10* (2013.01); *C08K 5/005* (2013.01)

(58) Field of Classification Search
CPC ..... C08K 5/005; C08K 5/1545; C07D 493/10
See application file for complete search history.

(56) References Cited

U.S. PATENT DOCUMENTS

| 3,989,698 A | 11/1976 | Jacobs et al. |
| 4,617,374 A | 10/1986 | Pruett et al. |
| 6,596,795 B2 | 7/2003 | Zhao et al. |

FOREIGN PATENT DOCUMENTS

| EP | 0 516 006 A1 | 12/1992 |
| WO | WO 2010/056452 A2 | 5/2010 |

OTHER PUBLICATIONS

Il'Ina, Irina, et al., "Highly potent analgesic activity of monoterpene-derived (2S,4aR,8R,8aR)-2-aryl-4,7-dimethyl-3,4,4a,5,8,8a-hexahydro-2H-chromene-4,8-diols," *Med Chem Res*, vol. 23, pp. 5063-5073 (2014).
XP002792419; Database accession No. 2233585-18-5; Database Registry [Online], Chemical Abstracts Service, Columbus, Ohio, US, 1 pg. (Aug. 1, 2018).

*Primary Examiner* — Angela C Scott
(74) *Attorney, Agent, or Firm* — Christensen, Fonder, Dardi & Herbert PLLC

(57) ABSTRACT

An ultraviolet (UV) absorbing compound and uses of the same are provided. The UV absorbing compound is represented by the following Formula I:

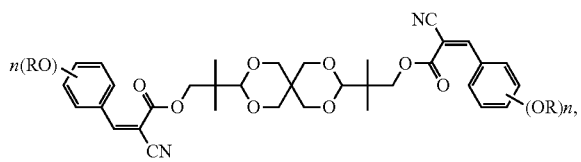

[Formula I]

in Formula I, each R is independently H, $C_1$-$C_{20}$ alkyl, glycidyl, or —$(CH_2CH_2O)_m$—$(CH_2)_p$—$CH_3$, wherein m is an integer of 1 to 20, p is an integer of 0 to 20, and n is an integer of 0 to 3.

16 Claims, 1 Drawing Sheet

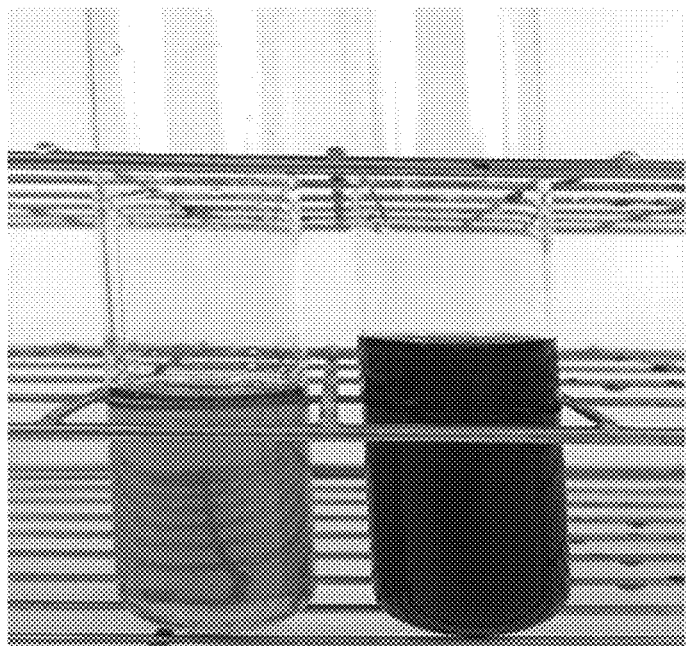
UV absorbing compound Ia    Clearshield 390

ULTRAVIOLET ABSORBING COMPOUND AND APPLICATIONS THEREOF

CLAIM FOR PRIORITY

This application claims the benefit of Taiwan Patent Application No. 107121886 filed on Jun. 26, 2018, the subject matters of the applications are incorporated herein in their entirety by reference.

BACKGROUND OF THE INVENTION

Field of the Invention

The present invention provides an ultraviolet (UV) absorbing compound and applications thereof. The UV absorbing compound has a light color and excellent thermal stability and is useful for various technical fields requiring resistance to UV rays, including but are not limited to sunscreen products, plastics, rubber, paints, and dyes.

Descriptions of the Related Art

UV absorbers are utilized for absorbing UV rays, which are harmful and cause degradation of materials such as polymers. Benzotriazoles, benzophenones and triazines are the best known commercially available UV absorbers; however, they only are useful in absorbing UV rays with wavelengths from 260 to 360 nm and cannot effectively absorb UV rays with wavelengths from 350 to 400 nm (i.e., UV-A rays). Products using such UV absorbers, such as transparent plastic containers for food or medicine, will still degrade under the exposure of near-visible UV rays with wavelengths from 350 to 400 nm. Although several complex triazines and benzotriazoles can absorb UV rays with wavelengths up to 400 nm, they are so limited in application due to cost and other factors.

U.S. Pat. No. 3,989,698 discloses a UV absorber which belongs to benzoxazines and has been commercialized as Cyasorb UV-3638. The UV absorber can be added to, for example, polyethylene terephthalate (PET) or polycarbonate (PC) to make the container manufactured therefrom be able to block UV rays with wavelengths below 370 nm and thus protect the UV-sensitive components therein. However, a UV absorber for UV rays with wavelengths of 400 nm or up to 420 nm is still required because many nutritional ingredients and natural dyes are also sensitive to UV rays with wavelengths from 370 to 400 nm.

U.S. Pat. No. 4,617,374 discloses a methine-containing compound with the following structure:

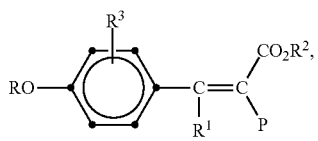

the compound can react with polyesters and polycarbonates as a chain terminator to provide UV protection. However, the UV protection applies to only UV rays with wavelengths from 320 to 380 nm and cannot cover all near-visible UV rays with wavelengths from 350 to 400 nm.

U.S. Pat. No. 6,596,795 B2 also discloses a vanillin-modified UV absorber which is represented by the following formula and has been commercialized as Clearshield 390:

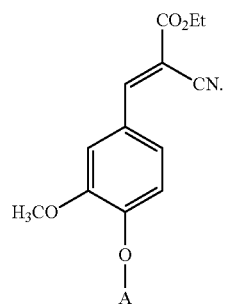

In the above formula, A is a polyether-polyol group. The UV absorber can absorb UV rays with wavelength from 320 to 400 nm. However, the UV absorber is a dark liquid and has poor thermal stability. The UV absorber is not suitable for products requiring color accuracy or involving a high processing temperature. In addition, the UV absorber is modified with a polyether-polyol group with a large molecular weight, which lowers the UV absorption ability per unit weight of the UV absorber. As a result, the UV absorber must be used in a higher amount, resulting in increased costs.

WO 2010/056452 A2 further improves the UV absorber of U.S. Pat. No. 6,596,765 B2 and provides the following UV absorber (1) and UV absorber (2):

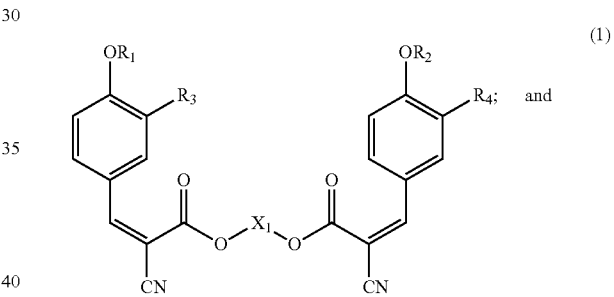

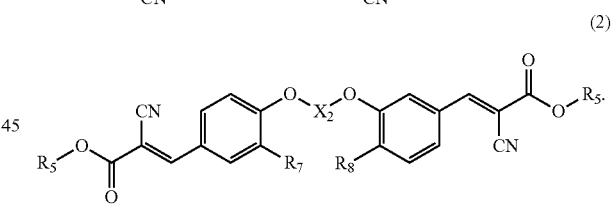

The UV absorber (1) is a dimer connected by ester groups. The UV absorber (2) is a dimer connected by ether groups, and can also absorb UV rays with wavelengths from 320 to 400 nm. However, a mixing test with polypropylene (PP) shows that the color of the obtained specimen is partially yellow and more intense than the yellow in Clearshield 390. The results show that the UV absorbers (1) and (2) still have insufficient thermal stability, although they have increased molecular weight by forming a dimer.

SUMMARY OF THE INVENTION

In view of the abovementioned technical problems of conventional UV absorbers, the present invention provides a UV absorbing compound which is a yellowish solid at normal temperature and pressure. In comparison with a liquid UV absorber, the UV absorbing compound of the present invention is advantageous in that the UV absorbing compound of the present invention can be purified by crystallization to reduce color and improve impurity and compatibility with plastic. The UV absorbing compound is a useful UV absorber that can absorb UV rays including 320 to 400 nm UV-A rays. Furthermore, the UV absorbing compound of the present invention can be used in engineering plastics involving high processing temperatures, like PET, PC, polyamide, etc., by virtue of its high thermal stability. In addition, the UV absorbing compound of the present invention surprisingly can improve the yellowing of plastic that occurs after processing. Accordingly, the present invention involves at least the objectives described below.

An objective of the present invention is to provide a UV absorbing compound, which is represented by the following Formula I:

Another objective of the present invention is to provide a method of absorbing UV rays by using the aforementioned UV absorbing compound as a UV absorber.

Yet another objective of the present invention is to provide a UV resistant material, comprising a base material, and a first UV absorber which is the aforementioned UV absorbing compound.

In some embodiments of the present invention, the UV resistant material further comprises a second UV absorber selected from the group consisting of benzotriazoles, benzoxazinones, triazines, and combinations thereof.

In some embodiments of the present invention, the base material of the UV resistant material is a polymer, such as a polymer selected from the group consisting of polyethyl-

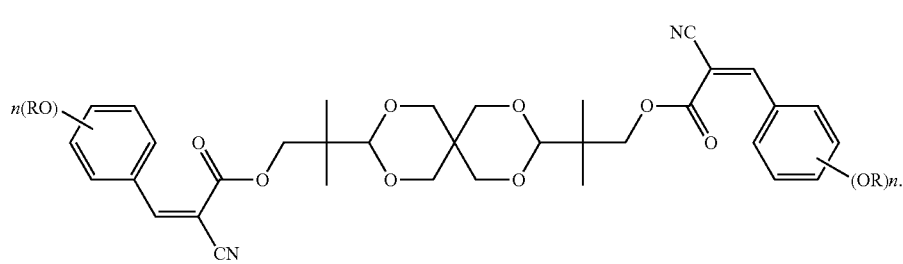

[Formula I]

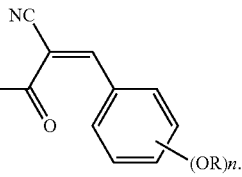

In formula I, each R is independently H, $C_1$-$C_{20}$ alkyl, glycidyl, or —$(CH_2CH_2O)_m$—$(CH_2)_p$—$CH_3$, wherein m is an integer of 1 to 20 and p is an integer of 0 to 20; and n is an integer of 0 to 3. More specifically, each R is independently $C_1$-$C_6$ alkyl, or —$(CH_2CH_2O)_m$—$(CH_2)_p$—$CH_3$, wherein m is an integer of 1 to 6 and p is an integer of 0 to 6; and n is 2 or 3.

In some embodiments of the present invention, each R is independently $C_1$-$C_6$ alkyl, and n is 2.

In some embodiments of the present invention, the UV absorbing compound is represented by the following Formula Ia or Formula Ib:

ene terephthalate, polycarbonate, polypropylene, polyethylene (PE), polyamide, and combinations thereof.

In some embodiments of the present invention, the UV resistant material further comprises a component selected from the group consisting of antioxidants, antistatic agents, antihydrolysis agents, tougheners, colorants, fillers, flame retardants, and combinations thereof.

To render the above objectives, technical features and advantages of the present invention more apparent, the present invention will be described in detail with reference to some embodiments hereinafter.

[Formula Ia]

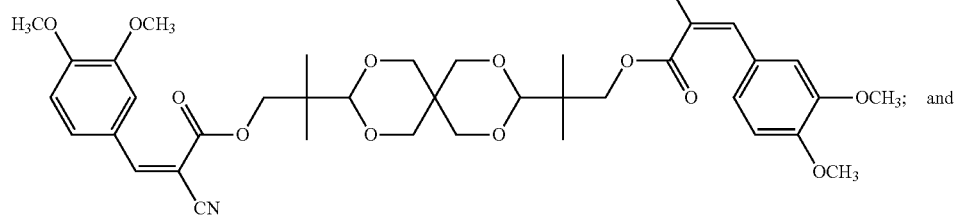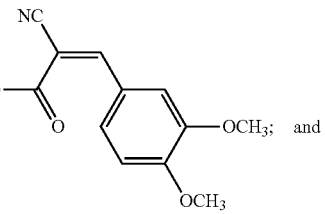

and

[Formula Ib]

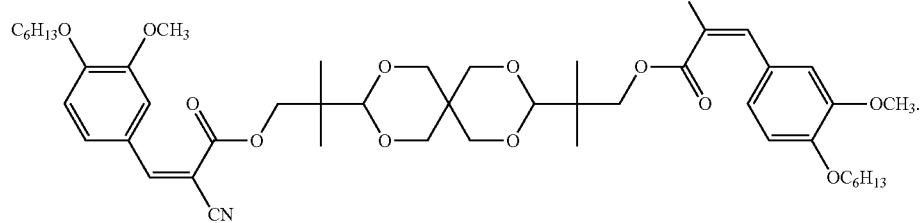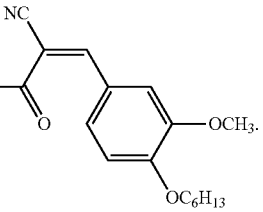

BRIEF DESCRIPTION OF THE DRAWINGS

FIG. 1 shows a photograph of the appearance of each of UV absorbing compound Ia according to the present invention and Clearshield 390 after a heat treatment at 240° C. for 10 minutes.

DESCRIPTION OF THE PREFERRED EMBODIMENT

Hereinafter, some embodiments of the present invention will be described in detail. However, without departing from the spirit of the present invention, the present invention may be embodied in various embodiments and should not be limited to the embodiments described in the specification.

Unless it is additionally explained, the expressions "a," "the," or the like recited in the specification (especially in the claims) should include both the singular and the plural forms.

Unless it is additionally explained, the expressions "first," "second," or the like is used to distinguish different elements or components, not terms supplying a numerical limit.

Unless it is additionally explained, the expression "alkyl" recited in the specification (especially in the claims) includes linear, branched and/or cyclic alkyl groups. The configuration of any carbon-carbon double bond appearing herein is selected for convenience only and is not intended to designate a particular configuration; thus a carbon-carbon double bond depicted arbitrarily herein as (Z) may be (Z), (E), or a mixture of the two in any proportion.

Ultraviolet (UV) Absorbing Compound

The UV absorbing compound of the present invention is represented by the following Formula I:

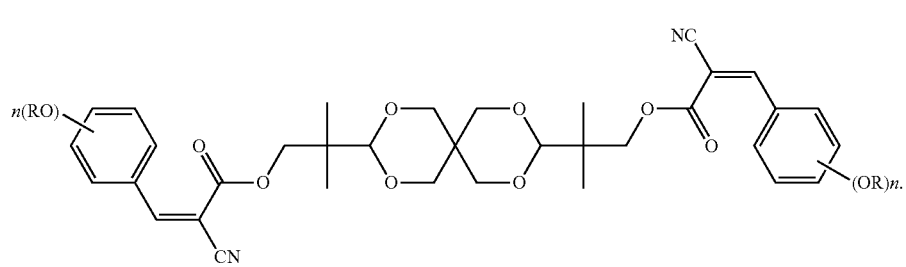

[Formula I]

In formula I, each R is independently H, $C_1$-$C_{20}$ alkyl, glycidyl, or —$(CH_2CH_2O)_m$—$(CH_2)_p$—$CH_3$, wherein m is an integer of 1 to 20 and p is an integer of 0 to 20; and n is an integer of 0 to 3. In terms of the thermal stability and the UV absorbing ability per unit weight, each R in formula I is independently preferably $C_1$-$C_{20}$ alkyl, and more preferably $C_1$-$C_6$ alkyl.

In some embodiments of the present invention, each R in formula I is independently $C_1$-$C_6$ alkyl, or —$(CH_2CH_2O)_m$—$(CH_2)_p$—$CH_3$, wherein m is an integer of 1 to 6 and p is an integer of 0 to 6, and n in formula I is 2 or 3. In the appended examples, the UV absorbing compound is represented by the following Formula Ia or Formula Ib:

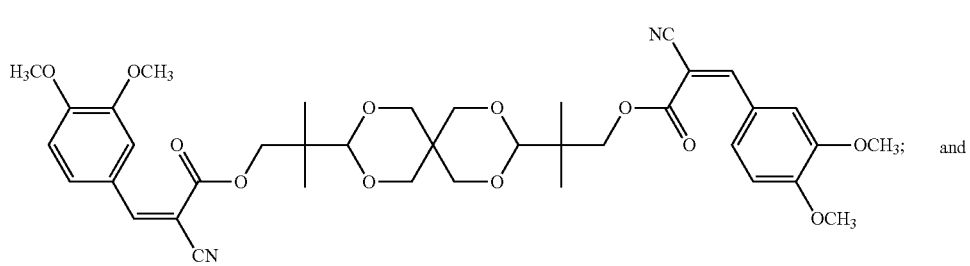

[Formula Ia]

and

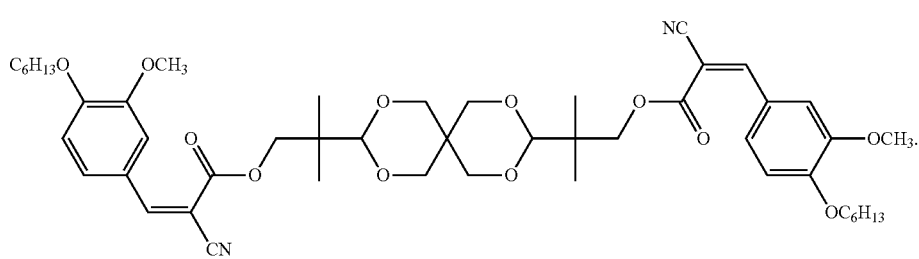

[Formula Ib]

The synthesis of the UV absorbing compound of the present invention is provided in the appended examples.

Applications of UV Absorbing Compound

The UV absorbing compound of the present invention can absorb UV rays and thus can be used as a UV absorber to improve UV resistance. The UV absorbing compound can be used either alone or in combination with other absorbers. Therefore, the UV absorbing compound of the present invention is useful for various technical fields requiring resistance to UV rays, including but are not limited to sunscreen products, plastics, rubber, paints, and dyes.

In some embodiments of the present invention, a UV resistant material is provided. The UV resistant material comprises a base material, the compound of the aforementioned formula I as a first UV absorber, and an optional second UV absorber.

The species of the base material is not particularly limited and, for example, can be a polymer. Examples of the polymer include polyethylene terephthalate (PET), polycarbonate (PC), polypropylene (PP), polyethylene (PE), polyamide (PA), and combinations thereof. In the appended examples, the base material is polyethylene terephthalate.

The species of the optional second UV absorber is not particularly limited, and can be selected by persons having ordinary skill in the art depending on the need. Examples of the second UV absorber include but are not limited to benzotriazoles, benzoxazines, triazines, and combinations thereof.

In the UV resistant material of the present invention, the amount of the first UV absorber or the optional second UV absorber are not particularly limited and can be adjusted by persons having ordinary skill in the art depending on the need, such as the desired UV resistance and cost. For example, when the first UV absorber is used in the UV resistant material alone, based on the total weight of the base material and the first UV absorber, the amount of the first UV absorber usually ranges from 0.01 wt % to 5 wt %, such as 0.05 wt %, 0.1 wt %, or 0.15 wt %. In some embodiments of the present invention, based on the total weight of the base material and the first UV absorber, the amount of the first UV absorber ranges from 0.075 wt % to 0.5 wt %.

In the UV resistant material of the present invention, the first UV absorber and the optional second UV absorber may be added to the base material in any manner that can realize UV protection to the base material. For example, the first UV absorber and the optional second UV absorber can be applied to the light receiving surface of the base material directly or by using a medium, or alternatively, the first UV absorber and the optional second UV absorber can be mixed with base material in such a way that the UV absorbers are dispersed between the molecules of the base material. For example, if the base material is a polymer, the base material together with the first UV absorber and the optional second UV absorber can be mixed and processed in a mixer to obtain the UV resistant material of the present invention. Given that persons having ordinary skill in the art will be able to perform the addition of UV absorbers based on the specification, especially the appended examples, the details of the addition of UV absorbers are not discussed here.

The UV resistant material of the present invention may further comprise one or more additives to improve the physicochemical properties of the base material. Examples of the additive include but are not limited to an antioxidant, an antistatic agent, an antihydrolysis agent, a toughener, a colorant, a filler, and a flame retardant. Use of additives is a general technique to persons having ordinary skill in the art and thus is not further discussed here.

The present invention is further illustrated by the following embodiments.

EXAMPLES

Example 1: Preparation of UV Absorbing Compound Represented by Formula Ia 200 g 3,4-dimethoxybenzaldehyde, 141 g ethyl cyanoacetate, 6.5 g ammonium acetate and 400 g xylene were added in sequence to a 2000 mL three-necked flask at room temperature with stirring. The obtained mixture was heated up to 140° C. under reflux for 8 hours, and water formed was removed by Dean-Stark. The reaction was monitored by Gas Chromatography (GC). After the reaction was completed, the mixture was allowed to cool, and the precipitate was collected by filtration and then dried to obtain the following compound a as a light yellow solid. The yield was 95%.

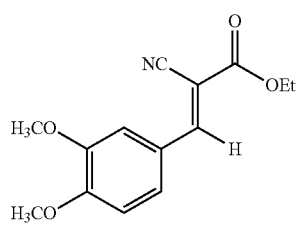

[Compound a]

200 g compound a obtained from previous step, 115 g spiroglycol, 3 g titanium triisopropoxide and 800 g xylene were added in sequence to a 2000 mL three-necked flask at room temperature with stirring by Dean-Stark. The obtained mixture was heated up to 140° C. under reflux for 12 hours, and ethanol was removed. The reaction was monitored by High Performance Liquid Chromatography (HPLC). After the reaction was completed, the mixture was allowed to cool, and the precipitate was collected by filtration and then dried to obtain the following UV absorbing compound Ia as a bright yellow solid. The yield was 95%.

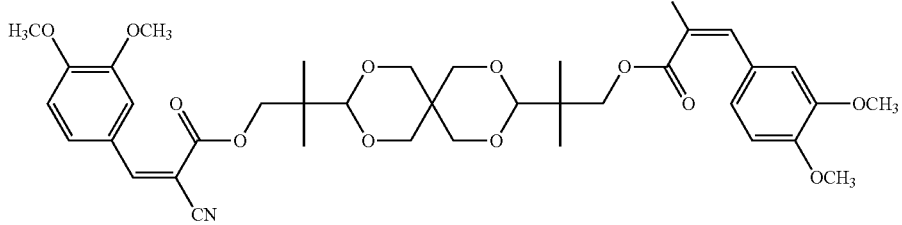

[UV absorbing compound Ia]

The UV absorbing compound Ia was subjected to nuclear magnetic resonance analysis, elementary analysis and melting point analysis. The results are as follows:

Nuclear magnetic $^1$H NMR (500 MHz, CDCl$_3$): 8.14 (s, 2H), 7.80 (s, 2H), 7.47 (d, 2H, resonance analysis: J=8.5 MHz), 6.95 (d, 2H, J=8.5 MHz), 4.52 (d, 2H, J=11.5 MHz), 4.36 (s, 2H), 4.16-4.10 (m, 4H), 3.96 (s, 6H), 3.95 (s, 6H), 3.59-3.52 (m, 4H), 3.35 (d, 2H, J=11.5 MHz), 1.02 (s, 12H)

$^{13}$C NMR (500 MHz, CDCl$_3$): 163.05, 154.83, 153.83, 149.40, 128.03. 124.72, 116.43, 111.73, 111.07, 104.80, 99.33, 71.26, 70.74, 70.25, 56.25, 56.12, 38.88, 32.68, 19.50, 19.45

Elementary analysis: Theoretical value: C %=63.75, H %=6.31, N %=3.81, O %=26.13;

Experimental value: C %=62.80, H %=6.52, N %=3.87, O%=26.90

Melting point analysis: 201 to 205° C.

Example 2: Preparation of UV Absorbing Compound Represented by Formula Ib 258 g compound b shown below, 115 g spiroglycol, 3 g titanium triisopropoxide and 800 g xylene were added in sequence to a 2000 mL three-necked flask at room temperature with stirring. The obtained mixture was heated up to 140° C. under reflux for 12 hours, and ethanol was removed. The reaction was monitored by High Performance Liquid Chromatography (HPLC). After the reaction was completed, the mixture was allowed to cool, and the precipitate was collected by filtration and then dried to obtain the following UV absorbing compound Ib as a bright yellow solid. The yield was 70%. The preparation of compound b can refer to Medicinal Chemistry Research, 23(12), 5063-5073, 2014.

$^{13}$C NMR (500 MHz, CDCl$_3$): 163.20, 154.97, 153.63, 149.64, 128.07, 124.44, 116.55, 112.11, 112.04, 104.83, 99.00, 56.18, 38.92, 32.72, 31.65, 28.98, 25.69, 22.68, 19.54, 19.47, 14.13

Melting point analysis: 120 to 126° C.

Example 3: Color Stability Test

The UV absorbing compound Ia and Clearshield 390, available from Milliken & company, were subjected to an exposure of 10 minutes at 240° C. to observe the color change. The Gardner color and appearance of each of UV absorbing compound Ia and Clearshield 390 after the exposure are shown in the following Table 1 and FIG. 1.

TABLE 1

| Gardner color after a 10-minute exposure at 240° C. | |
|---|---|
| Testing sample | Gardner color |
| UV absorbing compound Ia | 8.8 |
| Clearshield 390 | 18.8 |

As shown in Table 1 and FIG. 1, the color of UV absorbing compound Ia of the present invention remains the same yellowish color after a 10-minute exposure at 240° C. By contrast, the color of Clearshield 390 changes from yellow to dark brown. The results show that the UV absorbing compound Ia is significantly better than Clearshield 390 in terms of thermal stability, which ensures its applications in engineering plastics involving high processing temperature.

[Compound b]

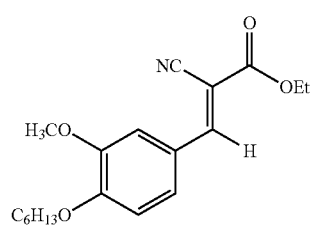

[UV absorbing compound Ib]

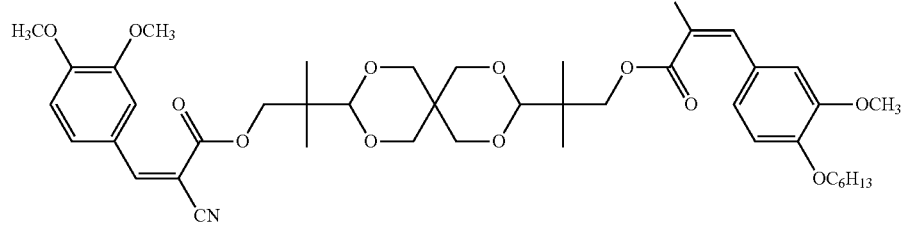

The UV absorbing compound Ib was subjected to nuclear magnetic resonance analysis and melting point analysis. The results are as follows:

Nuclear magnetic $^1$H NMR (500 MHz, CDCl$_3$): 8.13 (s, 2H), 7.79 (s, 2H), 7.47 (d, 2H, resonance analysis: J=8.5 MHz), 6.92 (d, 2H, J=8.5 MHz), 4.52 (d, 2H, J=11.5 MHz), 4.36 (s, 2H), 4.15-4.08 (m, 8H), 3.93 (s, 6H), 3.59-3.52 (m, 4H), 3.35 (d, 2H, J=11.5 MHz), 1.87 (quin, 4H), 1.46 (quin, 4H), 1.36-1.33 (m, 12H), 1.03 (s, 6H), 1.02 (s, 6H), 0.90 (q, 6H)

Example 4: Thermogravimetric Analysis (TGA) Test

UV absorbing compound Ia and Clearshield 390 were subjected to thermogravimetric analysis using a thermogravimetric analyzer (TGA) respectively. The temperature at which 10% weight loss occurred was recorded and shown in the following Table 2.

TABLE 2

| 10% weight loss temperature | |
|---|---|
| Testing sample | 10% weight loss temperature (° C.) |
| UV absorbing compound Ia | 402 |
| Clearshield 390 | 257 |

As shown in Table 2, the 10% weight loss temperature of UV absorbing compound Ia of the present invention is over 400° C., significantly higher than the processing temperature of general polymers, which shows that the UV absorbing compound of the present invention has a wider processing window. By contrast, the 10% weight loss temperature of Clearshield 390 is 257° C., which is insufficient for several plastics involving high processing temperature, such as PET, PC, PA and the like. If used in such plastics, Clearshield 390 may be pyrolyzed during processing, making the processing more difficult.

Example 5: Polyester Resin Specimen Experiment 100 parts by weight of polyethylene terephthalate granules are well mixed with 750 ppm of UV absorbing compound Ia or 1500 ppm of Clearshield 390 to provide a polyethylene terephthalate composition. Each polyethylene terephthalate composition was subjected to mixing at 280° C., and then the obtained granules were injected into a specimen at 280° C. The initial yellowing index (YI) of each specimen was measured and shown in the following Table 3. Then each specimen was subjected to an aging test (Q-SUN and QUV), and after 500 hours irradiation, transmittance (T %) at 400 nm of each specimen was measured by a UV-Vis spectrophotometer (CARY 50) and shown in the following Table 4.

TABLE 3

| Initial yellowing index of polyester specimen | |
|---|---|
| Polyethylene terephthalate specimen | YI |
| Adding 750 ppm of UV absorbing compound Ia | 5.5 |
| Adding 1500 ppm of Clearshield 390 | 7.3 |

TABLE 4

| Transmittance (T %) at 400 nm of polyester specimen after 500 hours irradiation | | |
|---|---|---|
| Polyethylene terephthalate specimen | Q-SUN | QUV |
| Adding 750 ppm of UV absorbing compound Ia | 8.75 | 4.06 |
| Adding 1500 ppm of Clearshield 390 | 8.17 | 4.46 |

As shown in Table 3, the yellowing index of the specimen using 750 ppm of UV absorbing compound Ia is lower than the other. Also, as shown in Table 4, according to the aging test, the UV protection performance at 400 nm of UV absorbing compound Ia is comparable to that of Clearshield 390, although UV absorbing compound Ia is half as much as Clearshield 390. Obviously, the UV absorbing compound Ia of the present invention shows excellent performance.

The above examples are used to illustrate the principle and efficacy of the present invention and show the inventive features thereof. People skilled in this field may proceed with a variety of modifications and replacements based on the disclosures and suggestions of the invention as described without departing from the principle and spirit thereof. Therefore, the scope of protection of the present invention is that as defined in the claims as appended.

What is claimed is:

1. An ultraviolet (UV) absorbing compound, which is represented by the following Formula I:

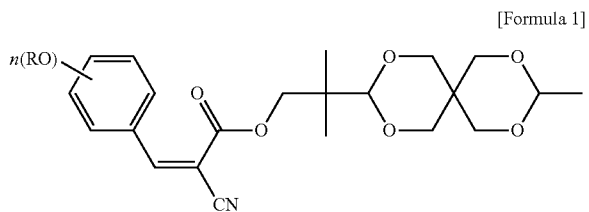

[Formula 1]

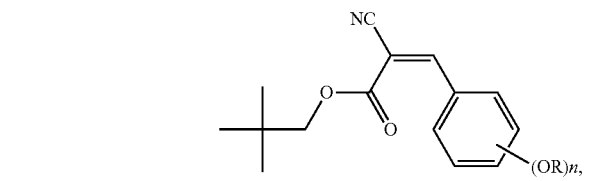

wherein, in Formula I, each R is independently $C_1$-$C_6$ alkyl or —$(CH_2CH_2O)_m$—$(CH_2)_p$—$CH_3$, wherein m is an integer of 1 to 6 and p is an integer of 0 to 6; and n is 2 or 3.

2. The compound of claim 1, wherein each R is independently $C_1$-$C_6$ alkyl, and n is 2.

3. The compound of claim 2, which is represented by the following Formula Ia or Formula Ib:

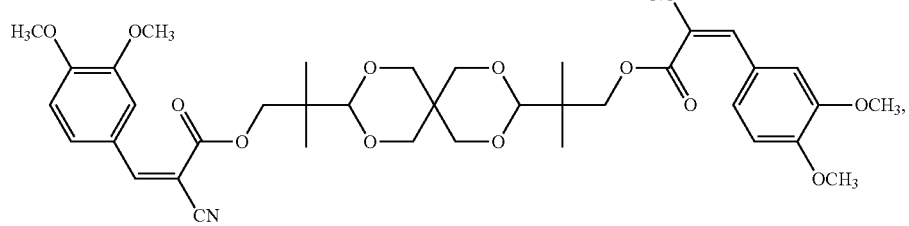

[Formula Ia]

-continued

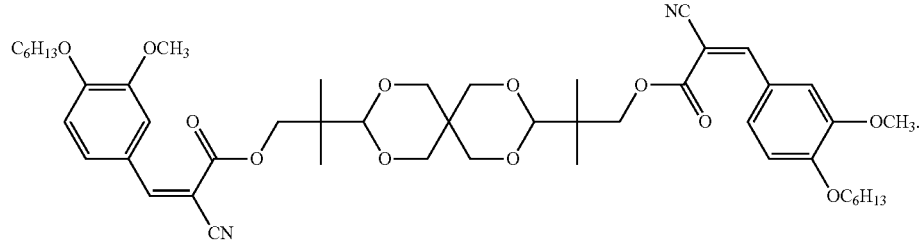
[Formula Ib]

4. A method of absorbing ultraviolet rays by using the ultraviolet absorbing compound of claim 1 as an ultraviolet absorber.

5. The method of claim 4, wherein, in Formula I, each R is independently $C_1$-$C_6$ alkyl, and n is 2.

6. The method of claim 5, wherein the ultraviolet absorbing compound is represented by the following Formula Ia or Formula Ib:

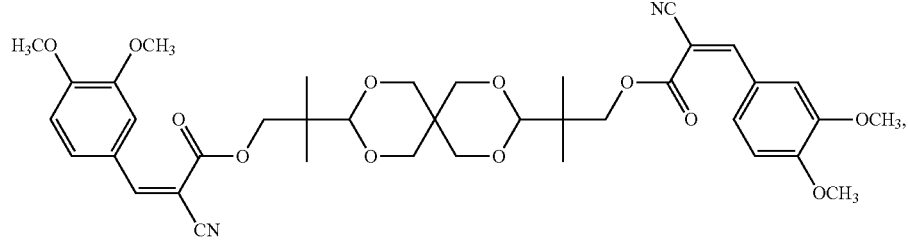
[Formula Ia]

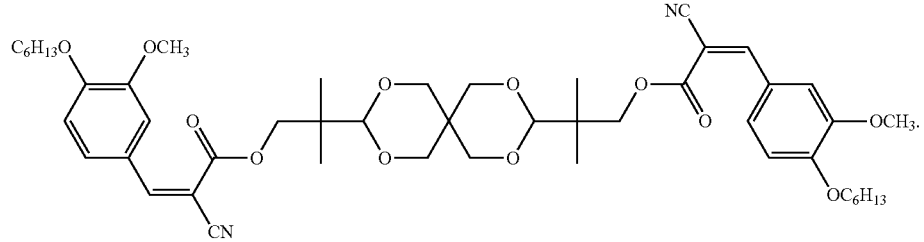
[Formula Ib]

7. An ultraviolet resistant material, comprising:
a base material; and
a first ultraviolet absorber, which is the ultraviolet absorbing compound of claim 1.

8. The ultraviolet resistant material of claim 7, wherein, in Formula I, each R is independently $C_1$-$C_6$ alkyl, and n is 2.

9. The ultraviolet resistant material of claim 8, wherein the ultraviolet absorbing compound is represented by the following Formula Ia or Formula Ib:

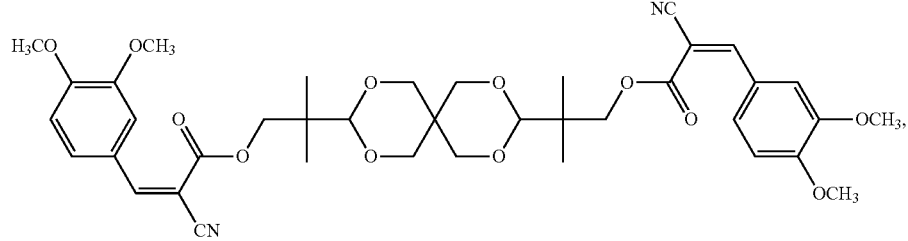
[Formula Ia]

-continued

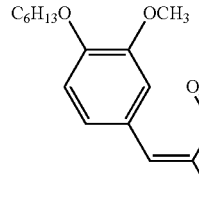 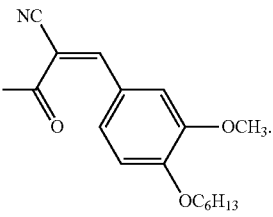

[Formula Ib]

10. The ultraviolet resistant material of claim 7, further comprising a second ultraviolet absorber selected from the group consisting of benzotriazoles, benzoxazinones, triazines, and combinations thereof.

11. The ultraviolet resistant material of claim 10, wherein the base material is a polymer.

12. The ultraviolet resistant material of claim 11, wherein the base material is selected from the group consisting of polyethylene terephthalate, polycarbonate, polypropylene, polyethylene, polyamide, and combinations thereof.

13. The ultraviolet resistant material of claim 10, further comprising a component selected from the group consisting of antioxidants, antistatic agents, antihydrolysis agents, tougheners, colorants, fillers, flame retardants, and combinations thereof.

14. The ultraviolet resistant material of claim 7, wherein the base material is a polymer.

15. The ultraviolet resistant material of claim 10, wherein the base material is selected from the group consisting of polyethylene terephthalate (PET), polycarbonate (PC), polypropylene (PP), polyethylene (PE), polyamide (PA), and combinations thereof.

16. The ultraviolet resistant material of claim 7, further comprising a component selected from the group consisting of antioxidants, antistatic agents, antihydrolysis agents, tougheners, colorants, fillers, flame retardants, and combinations thereof.

* * * * *